United States Patent [19]

Seebach et al.

[11] Patent Number: 4,585,892
[45] Date of Patent: Apr. 29, 1986

[54] PROCESS FOR THE ENANTIOSELECTIVE PRODUCTION OF α-ALKYLATED, ACYCLIC α-AMINOCARBOXYLIC ACIDS

[75] Inventors: Dieter Seebach; Reto Naef, both of Zurich, Switzerland

[73] Assignee: Degussa Aktiengesellschaft, Frankfurt am Main, Fed. Rep. of Germany

[21] Appl. No.: 654,935

[22] Filed: Sep. 27, 1984

[30] Foreign Application Priority Data

Sep. 27, 1983 [DE] Fed. Rep. of Germany ....... 3334855

[51] Int. Cl.[4] ............................................. C07C 99/00
[52] U.S. Cl. .......................................... 562/443; 548/301;
562/574; 562/575; 562/442; 562/440; 562/426;
562/556; 562/444; 564/193; 564/278
[58] Field of Search ................ 564/193, 278; 562/442,
562/443, 444, 574, 575, 440, 426, 556; 548/301

[56] References Cited

U.S. PATENT DOCUMENTS

| 3,721,679 | 3/1973 | Singer | 548/301 |
| 3,835,191 | 9/1974 | Wagner et al. | 564/278 |
| 4,275,217 | 6/1981 | Duhamel et al. | 564/278 |

Primary Examiner—James H. Reamer
Attorney, Agent, or Firm—Cushman, Darby & Cushman

[57] ABSTRACT

α-Alkylated, acyclic α-aminocarboxylic acids of the formula

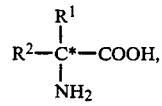

where * represents a center of asymmetry, $R^1$ is a lower alkyl, allyl, benzyl or substituted benzyl group and $R^2$ is a lower alkyl, methoxymethyl, lower alkylmercaptoethyl, phenyl, phenyl substituted with alkyl or alkoxy, benzyl, or benzyl substituted with alkyl, alkoxy or halo are produced by an enantio-selective plural step process from the corresponding α-aminocarboxylic acid monomethyl or monoethyl amide. A particular advantage of the new process is that there can be produced from one educt-enantiomer, i.e. from an (S)- or an (R)-α-aminocarboxylic acid, selectively depending on the reaction conditions used the two enantiomeric forms of the desired α-alkyl-α-aminocarboxylic acid.

20 Claims, No Drawings

PROCESS FOR THE ENANTIOSELECTIVE PRODUCTION OF α-ALKYLATED, ACYCLIC α-AMINOCARBOXYLIC ACIDS

SUMMARY OF THE INVENTION

The invention is directed to a new process for the enantioselective production of α-alkylated, acyclic α-aminocarboxylic acids of the formula:

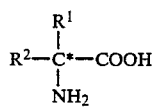
(I)

in which * is a center of asymmetry, R¹ is a methyl-,, ethyl-, n-propyl-, n-butyl-, allyl-, benzyl-, or substituted benzyl group and R² is a methyl-, ethyl-, n-propyl-, i-propyl-, n-butyl, secondary butyl-, i-butyl-, methoxymethyl-, methylmercaptomethyl-, 2-methyl-mercaptoethyl-, 2-ethylmercaptoethyl-, phenyl- or benzyl-group or a phenyl group substituted in any ring position with 1 to 3 alkyl or alkoxy groups or a benzyl group substituted in any ring position with 1 to 3 alkyl groups, alkoxy groups, fluorine or chlorine which comprises acid saponifying an imidazolidin-4-one of the formula

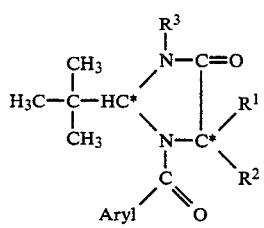
(II)

in which *, R¹ and R² are as defined above and R³ is a methyl or ethyl group and aryl is a phenyl or substituted phenyl group, e.g. alkyl or alkoxy substituted phenyl.

The alkyl and alkoxy groups attached to the phenyl and benzyl groups in formulae (I) and (II) for example can be methyl,, ethyl, propyl, isopropyl, butyl, sec.butyl, amyl, hexyl, methoxy, ethoxy, propoxy, or butoxy.

Finally the process of the invention starts from enantiomerically pure acyclic α-aminocarboxylic acids, requires no additional chiral auxiliaries, for example, a second optically active α-aminocarboxylic acid or optically active phenylethylamine and makes it possible to produce, i.e. from an (S)- or an (R)-α-aminocarboxylic acid, seletively the two enantiomeric forms of the desired α-alkyl-α-aminocarboxylic acid.

To carry out the process of the invention there is first converted an (S) or (R)-α-aminocarboxylic acid of the formula

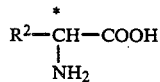
(IX)

in which * is a center of asymmetry and R² is a methyl-, ethyl-, n-propyl-, i-propyl-, n-butyl-, secondary butyl-, i-butyl-, methoxymethyl-, methylmercaptomethyl-, 2-methylmercaptoethyl-, 2-ethylmercaptoethyl-, phenyl-, benzyl- or a phenyl or benzyl group substituted at any ring position with 1 to 3 alkyl or alkoxy groups or a benzyl group substituted with fluorine or chlorine by reacting in known manner one of its esters with a lower alkanol, especially methanol or ethanol, with monoethylamine, or preferably monomethylamine to form the corresponding α-aminocarboxylic acid amide of the formula

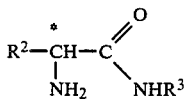
(VIII)

where * and R² are as defined above and R³ is a methyl or ethyl group.

As starting (S)- or (R)-α-aminocarboxylic acids of formula (IX) there can be used for example alanine, phenylanine, substituted phenylalanine such as 3,4-dimethoxyphenylalanine, phenylglycine, substituted phenylglycine such as 4-methoxyphenylglycine, 2-aminobutyric acid, valine, norvaline, leucine, isoleucine, norleucine, methionine, S-methylcysteine or O-methylserine.

The aminocarboxylic acid amide of formula (VIII) is then converted by condensation with pivalaldehyde into an imine (Schiff's base) of the formula

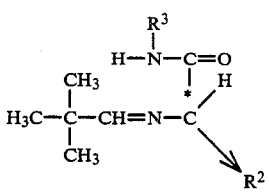
(VII)

in which *, R² and R³ are as defined above. The reaction is suitably carried out in such manner that the chiral α-aminocarboxylic acid amide of formula (VIII) together with pivalaldehyde are boiled in an inert solvent until complete elimination of water in a water separator. Suitable inert solvents for example are aliphatic or aromatic hydrocarbons, such as n-pentane,, n-hexane,, cyclohexane, benzene or toluene and halohydrocarbons, such as methylene chloride, chloroform or 1,2-dichloroethane. After separation of the eliminated water and the residual solvent there is obtained the imine of formula (VII) in very pure form and it can be reacted further directly without additional purification.

In this further reaction it is cyclized with simultaneous or subsequent introduction of the group

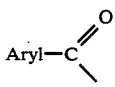

in which Aryl is a phenyl or substituted phenyl group. Depending on the reaction conditions used there is obtained in this cyclization reaction two difference diastereomers, since a second center of asymmetry is newly formed. If the imine of formula (VII) is reacted at a temperature between 110° and 150° C., preferably about 130° C. in the absence of a solvent with benzoic acid anhydride or a substituted benzoic acid anhydride there is obtained the corresponding imidazolidin-4-one of the formula

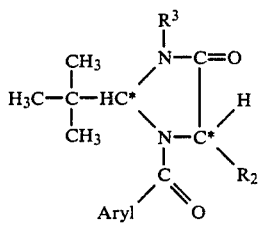
(V)

where *, $R^2$, $R^3$ and aryl are as defined above, in the cis form, in which the tert.butyl group and the substituted $R^2$ are in the cis form. The molar ratio of the benzoic acid anhydride employed to the imine of formula (VII) is suitably 1.0 to 1.2:1, preferably 1.1:1.

In contrast, if the imine of formula (VII) is reacted at relatively low temperature first with methanolic hydrochloric acid and then with a benzoyl halide, e.g. benzoyl chloride or benzoyl bromide, or a substituted benzoyl halide in the presence of tertiary amine, such as triethylamine or pyridine serving as an acid acceptor, then there is formed the corresponding imidazolidin-4-one of formula (V) in the trans-form, in which the tert.butyl group and the substituent $R^2$ are fixed as trans. The suitable temperatures for the reaction with the methanolic hydrochloric acid are between $-10°$ and $+40°$ C., preferably between 0° and $+25°$ C. The methanolic hydrochloric acid is used in excess (at least 5 molar, based on the imine employed) and the reaction requires a time between about 2 and 3 hours. Then the HCl/CH$_3$OH mixture is removed and the residue taken up in methylene chloride and treated with one equivalent of benzoyl halide and 2 equivalents of a tertiary amine. The most suitable temperatures for this reaction likewise are again between 0° and 25° C. The reaction mixture is neutralized with soda solution, the organic phase is concentrated under reduced pressure and the residue dried in a vacuum at a temperature between 30° and 60° C.

In the conversion of the amine of formula (VII) into the corresponding imidazolidine-4-one of formula (V) as benzoic anhydride or benzoyl halide there is preferably used the unsubstituted benzoic anhydride or benzoyl chloride. However, it should be understood that nuclear substituted benzoic anhydrides and nuclear substituted benzoyl halides, e.g. 4-methylbenzoic anhydride, 4-chlorobenzoic anhydride, 4-methylbenzoyl bromide, 4-chlorobenzoyl chloride, and 2-chlorobenzoyl chloride, can also be used.

The crude cis or trans imidazolidin-4-one obtained, if necessary, is further purified by recrystallization.

The imidazolidin-4-one of formula (V) in the cis or trans form is subsequently reacted with a strong base of the formula

M—Y (VI)

in which M is lithium, sodium, or potassium and Y is hydrogen or a n-butyl, tert.-butylate, amino, dimethylamino, diethylamino, di-n-propylamino, diisopropylamine, di-(trimethylsilyl)-amino or phenyl group. This reaction is suitably carried out in such manner that there is added the strong base of formula (VI) in an amount of 1.0 to 1.1 equivalents all at once or within a few minutes to a solution of the imidazolidin-4-one in an inert solvent. Suitable inert solvents for example are ethers, such as diethyl ether, di-n-propyl ether, methyl tert.butyl ether or tetrahydrofuran and also hydrocarbons, such as n-pentane, n-hexane or cyclohexane. Optionally there can also be employed mixtures of such ethers and hydrocarbons.

As the bases of formula (VI) there can be used for example butyl lithium, phenyl lithium, sodium hydride, potassium tert.butylate or N,N-disubstituted lithium amide. Preferred are butyl lithium and lithium diisopropyl amide. The most suitable reaction temperatures are between $-80°$ and 0° C.

In this reaction enolates of the formula

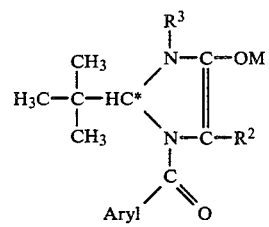
(III)

forms in which *, $R^2$, $R^3$, aryl and M are as defined above.

This enolate present in solution suitably, likewise again at a temperature between $-80°$ and 0° C., is further reacted with an alkylating agent of the formula $R^1$—X in which $R^1$ is a methyl, ethyl, n-propyl, n-butyl, allyl, benzyl or substituted benzyl group and X is a group which leaves of the group chloride, bromide, iodide, tosylate, mesylate, or trifluoromethylsulfonate. If $R^1$ is a substituted benzyl group this can be substituted in any ring position 1 to 3 times by fluorine, chlorine, bromine or a methoxy, ethoxy, methyl, ethyl or isopropyl group, e.g. 2-chlorobenzyl, 3-chlorobenzyl, 4-chlorobenzyl, 2,4-dichlorobenzyl, 2,4,5-trichlorobenzyl, 4-bromobenzyl, 2,4-dibromobenzyl, 4-fluorobenzyl, 2-fluorobenzyl, 2,4-difluorobenzyl, 4-methoxybenzyl, 3-methoxybenzyl, 4-ethoxybenzyl, 4-methylbenzyl, 2,4-dimethylbenzyl, 4-ethylbenzyl, 2-isopropylbenzyl.

The alkylating agent of formula (IV) is suitably used in a 1.1 to 1.2 fold molar excess, based on the original imidazolidin-4-one of formula (V) employed for formation of the enolate.

In the alkylation reaction there is formed an imidazolidin-4-one of the formula

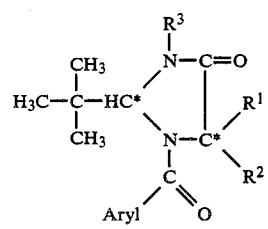
(II)

in which *, $R^1$, $R^2$, $R^3$ and aryl are as defined above.

The stereochemical course of the alkylation reaction is such that the tert.butyl group and the substituted $R^2$ in the imidazolidin-4-one of the formula (II) always are cis and the tert.butyl group and the newly introduced substituent $R^1$ always are trans. Because of the different configuration fo the carbon atoms carrying the tert.butyl group and the substituted $R^2$ in the imidazolidin-4-one of formula (V) ultimately there is produced starting from an enantiomer of one α-aminocarboxylic acid both enantiomeric forms of the α-alkyl-α-aminocarboylic acid to be produced.

The imidazolidin-4-one of formula (II) is finally saponified with acid to the α-alkylated, acylic α-aminocarboxylic acid of the formula

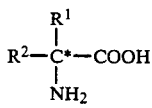

$$R^2-\overset{R^1}{\underset{NH_2}{\overset{|}{C^*}}}-COOH \quad (I)$$

in which *, $R^1$ and $R^2$ are as defined above. This occurs suitably through heating with a relatively concentrated mineral acid to a temperature between 150° and 200° C. under pressure (i.e. superatmospheric pressure). As acids above all, there are used 20 to 36 weight percent hydrochloric acid or 30 to 48 weight percent aqueous hydrobromic acid. There can also be used 10 to 50 weight percent aqueous sulfuric acid.

The hydrolysis mixture is cooled down, filtered, extracted with methylene chloride and the aqueous phase evaporated in a vacuum. The residue is taken up in water and in known manner freed from the mineral acid contained therein with the help of an ion exchanger or propylene oxide. The aqueous solution of the α-alkylated, acyclic α-aminocaraboxylic acid remaining of formula (I) is evaporated and dried to constant weight under reduced pressure. In this manner there are obtained the crystalline acids in good chemical yields and in optical yields of 90 to 95%.

Consequently the process of the invention opens an outstanding access to the α-alkylated, acyclic α-amonocarboxylic acids of formula (I). For example, in this way (−)-α-methyldopa, an important pharmaceutical, can be produced from (S)-alanine in simple manner. The chirality of the starting aminocarboxylic acid reproduces itself. Therefore there are not required additional optically active auxiliary reagents for the entire reaction sequence.

Unless otherwise indicated all parts and percents are by weight.

The process can comprise, consist essentially of, or consist of the stated steps with the recited materials.

The process of the invention is explained in more detail through the following examples.

DETAILED DESCRIPTION

Example 1

(a) Production of (S)-N-(2',2'-dimethyl-propylidene)-valine monomethylamide

There were added 95.7 ml (870 mmols) of pivalaldehyde to 112.0 grams (864 mmoles) of (S)-valine monomethylamide dissolved in 300 ml of n-pentane. The reaction mixture was boiled at a water separator until the formation of water was ended (4 hours). The solvent was removed under reduced pressure and there remained behind 130 grams (76% of theory) of (S)-N-(2',2'-dimethyl-propylidene)-valine monomethylamide, which could be further worked without purification. To ascertain the exact material data, a test of sample was purified by distillation.

Boiling Point: 80° C./0.013 mbar.
Melting Point: 69° C.

|  | % C | % H | % N |
|---|---|---|---|
| Calculated: | 66.62 | 11.18 | 14.13 |
| Found: | 66.78 | 11.11 | 14.17 |

IR (CDCl₃): 3400 (m), 2955 (s), 1665 (s), 1520 (m), 1460 (m), 1365 (m) cm$^{-1}$.

¹H-NMR (CDCl₃ 7.46 (s, 1H) C$\underline{H}$=N; 6.43 (s, 1H), NH; 3.23 (d, J=5 Hz, 1H) C$\underline{H}$—N; 2.77 (d, J=6 Hz, 3$\underline{H}$) CH₃—N; 2.16 (m, 1$\underline{H}$) CH—C; 1.13 (s, 9H) (C$\underline{H}_3$)₃—C; 0.87 ppm (d, J=6 Hz, 6H) (C$\underline{H}_3$)₂—C.

(b) Production of (2R,5S(-1-Benzoyl-2-tert.butyl-5-ethyl-ethyl-3-methyl-imidazolidine-4-one 52.0 grams (260 mmoles) of the (S)-N-(2',2'-dimethyl-propylidene)-valine monomethylamide produced according to (a) were heated with 64.6 grams (286 mmoles) of benzoic anhydride for one hour at 140° C. After cooling off the solidified mass was taken up in 500 ml of methylene chloride and the methylene chloride solution washed twice, each time with 300 ml of 2N soda solution and once with 200 ml of water. The organic phase was dried over MgSO₄ and the methylene chloride distilled off under reduced pressure. The residue was washed once with cold diethyl ether for purification. Yield of (2R,5S)-1-benzoyl-2-tert.butyl-5-(methylethyl)-3-methyl-imidazolidin-4-one, 66.6 grams (82% of theory).

Melting Point: 112° C.
[α]$_D^{25}$: +22.4° (c=1.7; CHCl₃).

|  | % C | % H | % H |
|---|---|---|---|
| Calculated: | 71.49 | 8.67 | 9.26 |
| Found: | 71.57 | 8.75 | 9.39 |

IR (CHCl₃): 2965 (m), 1685 (s), 1635 (s), 1362 (s), 1295 (m) cm$^{-1}$.

¹H-NMR (CCl₄): 7.46–7.13 (m, 5H) H$_{Ar}$; 5.33 (s, 1H) C$\underline{H}$; 3.86 (d, J=10 Hz,1H) CH—CH (CH₃)₂; 2.97 (s, 3$\underline{H}$) CH₃—N; 2.06–1.46 (m, 1$\underline{H}$) CH—CH (CH₃)₂; 1.03 (s, 9H) CH₃)₃—C; 1.00 (d, J=6 Hz, 3H) $\overline{HC}$—C$\underline{H}_3$; 0.66 ppm (d,J=6 Hz, 3H) HC—C$\underline{H}_3$.

(c) Production of (2R,5S)-1-Benzoyl-2-tert.butyl-3,5-dimethyl-5-(methylethyl)-imidazolidin-4-one There were added to 3.02 grams (10.0 mmoles) of the 2R,5S)-1-benzoyl-2-tert.butyl-5-(methylethyl)-3-methyl-imidazolidin-4-one produced according to (b) and dissolved in 60 ml of tetrahydrofuran at −78° C. 15 mmoles of methyl iodide. The reaction mixture as allowed to warm to room temperature. The now weakly yellow reaction mixture was poured into 100 ml of an about half saturated aqueous NH₄Cl solution and extracted with, in all, 200 ml of diethyl ether. The combined organic extracts were washed with water dried over MgSO₄ and freed from solvent under reduced pressure. For further purification the residue was chromatagraphed with a mixture of diethyl ether and n-pentane in a volume ratio of 5:1 as mobile phase. After the evaporation of the solvent from the eluate there remained behind 2.18 grams (70% of theory) of (2R,5S)-1-benzoyl-2-tert.butyl-3,5-dimethyl-5-(methylethyl)-imidazolidin-4-one.

[α]$_D^{25}$: +38.7° (c=1.4; CHCl₃).

¹H-NMH (CDCl₃): 7.43 (s,5H) H_Ar; 5.46 (s,1H) C—H; 3.00 (s,3H) CH₃—N; 2.26-1.76 (m,1H) C—CH [CH₃]₂; 1.37 (s, 3H) C—CH₃; 1.15 (d, J=7 Hz, 3H) CH (CH₃) and 1.12 (d, J=7 Hz, 3H) CH—(CH₃) 1.02 ppm (s, 9H) C—(CH₃)₃.

(d) Production of (S)-α-Methylvaline 1.36 grams (4.3 mmoles) of the (2R,5S)-1-benzoyl-2-tert.butyl-3,5-dimethyl-5-(methylethyl)-imidazolidin-4-one produced according to (c) were heated in a bomb tube at 180° C. for 4 hours with 30 ml of 20 weight percent aqueous hydrochloric acid. The hydrolysis mixture was filtered, extracted with 30 ml of methylene chloride and teh aqueous phase evaporated to dryness in a vacuum. The residue was taken up in 30 ml of water and dehydrohalogenated by means of an ion exchanger (Dowex 50 WX 8). The thus obtained aqueous solution of the free (S)-α-methylvaline was evaporated and the crystalline residue dried to constant weight at 50° C. in a vacuum. Yield 0.535 gram (95% of theory). $[\alpha]_D^{25}$: −4.3° (c=1; 0.2N HCl).

¹H-NMR (D₂O): 2.56-2.16 (septett, J=6 Hz,1H) CH (CH₃)₂; 1.65 (s, 3H) a—C—CH₃; 1.12 ppm (d, J=6 Hz,6H) CH—(CH₃)₂;
Reference (HDO): 4.90 ppm.

Example 2

(a) Production of (S)-N-(2',2'-Dimethylpropylidene)-methioninemonomethylamide

There were added 27.5 ml (250 mmoles) of pivalaldehyde to 40.0 grams (247 mmoles) of (S)-methionine monomethylamide dissolved in 100 ml of n-pentane. The reaction mixture was boiled on the water separator until the formation of water was ended (3 hours). The solvent was removed under reduced pressure and there remained behind 52.2 grams (92% of theory) of (S)-N-2',2'-dimethylpropylidene)-methionine monomethylamide which was further worked up without further purification. To ascertain the exact material data a test sample was purified by distillation.

Boiling Point: 120° C./0.13 mbar.
$[\alpha]_D^{25}$: +10.6° (c=2.4: CHCl₃).
IR (CHCl₃): 3400 (m), 2960 (s), 1665 (s), 1525 (m), 1365 (m) cm⁻¹.
MS: 215 (M⁺—15.1), 173 (100)
¹H-NMR (C Cl₄): 7.56 (s,H) CH=N; 6.56 (d, J=5 Hz, 1H) NH; 3.66 (dd, J₁=4 Hz, J₂=8 Hz,1H) C—H; 2.77 (d, J=5 Hz, 3H) CH₃—N; 2.57-1.56 (m, 4H) (CH₂)₂; 2.02 (s, 3H) CH₃—S; 1.10 ppm (s, 9H) (CH₃)₃C.

(b) Production of (2S,5S)-1-Benzoyl-2-tert.butyl-3-methyl-5-(3'-thiabutyl)-imidazolidin-4-one A solution of 23.0 grams (100.0 mmole) of the (S)-N-(2',2'-dimethylpropylidene)-methionine monomethylamide produced according to (a) and dissolved in 30 ml of methanol was treated with cooling to 0° C. with 60 ml of a saturated methanolic hydrochloric acid and stirred for 30 minutes at 0° C. and subsequently for 2 hours at 25° C. The solvent was removed at 25° C. under reduced pressure and the residue taken up in 100 ml of methylene chloride. The methylene chloride solution was treated at 0° C. with 11.6 ml (100 mmoles) of benzoyl chloride and 27.7 ml (200 mmoles) of triethylamine. After heating to 25° C. the reaction mixture was washed twice, each time with 150 ml of 2N soda solution (aqueous sodium carbonate) and once with 100 ml of water. The organic phase was dried over MgSO₄, the methylene chloride distilled off in a vacuum and the residue dried for 1 hour at 50° C. and 0.065 mbar. Yield of (2S,5S)-1-benzoyl-2-tert.butyl-3-methyl-5-(3'=thiabutyl)-imidazolidin-4-one. 31.5 grams (94% of theory). The product was recrystallized twice from diethyl ether for purification.

Melting Point: 129° C. $[\alpha]_D^{25}$: +58.8° (c=1.4; CHCl₃).
IR (CHCl₃): 2970 (m), 1690 (s), 1650 (s), 1365 (s), 1110 (m) cm⁻¹.
MS: (M⁺, 1), 278 (100).
¹H-NMR (CDCl₃): 7.93-7.30 (m, 5H) H_Ar; 5.66 (s,1H) c—H; 4.42 (d, J=5 Hz,1H) CH—CH₂)₂—S—CH₃; 3.06 (s,3H) CH₃—N; 3.00-1.80 (m, 4H) (CH₂)₂—S— CH₃; 1.73 (s, 3H) CH₃—S; 1.06 ppm (s, 9H) (CH₃)₃—C.

Production of (2S,5R)-1-Benzoyl-2-tert.butyl-3,5-dimethyl-b 5-(3'-thiabutyl)-imidazolidin-4-one There were added at −60° C. 10.6 mmoles of a 1 molar solution of lithium diisopropylamide in tetrahydrofuran to 3.34 grams (10.0 mmoles) of the (2S,5S)-1-benzoyl-2-tert.butyl-3-methyl-5-(3'-thiabutyl)-imidazolidin)-4-one produced according to (b) and dissolved in 60 ml of tetrahydrofuran. Thereby the solution became deeply red in color. After stirring for a further 15 minutes at −60° C. there was added 0.9 ml (15.0 mmoles) of methyl iodide. The now weakly yellow reaction mixture was allowed to warm up to room temperature, poured into 100 ml of about half saturated aqueous NH₄Cl solution and extracted with, in all, 200 ml of diethyl ether. The combined organic extracts were washed with water, dried over MgSO₄ and freed from solvent under reduced pressure. The residue was recrystallized from a mixture of diethyl ether and n-pentane in the volumn ratio 1:1, where there were obtained 2.36 grams (66% of theory of (2S,5R)-1-benzoyl-2-tert-.butyl-3,5-(3'-thiabutyl)-imidazolidin-4-one.

Melting Point: 105° C.
$[\alpha]_D^{20}$: −71.9° (c=1; CHCl₃).
¹H-NMR (CDCl₃): 7.50 (s,5H) H_Ar; 5.83 (s, 1H) C—H; 3.84 (s, 3H) CH₃—N; 3.00-2.00 (m, 4H) (CH₂)₂; 2.03 (s, 3H) S—CH₃; 1.10 ppm (s,12H) C—CH₃ and (CH₃)₃—C.

(d) Production of (R)-α-Methylmethionine

There were heated at 180° C. for 4 hours in a bomb tube 1.0 gram (2.79 mmoles) of the (2S,5R)-1-benzoyl-2-tert.butyl-3,5-dimethyl-5-(3'-thiabutyl)-imidazolidin-4-one produced according to (c) together with 25 ml of 20 weight percent aqueous hydrochloric acid. The hydrolysis mixture was filtered, extracted with 30 ml of methylene chloride and the aqueous phase evaporated to dryness in a vacuum. The residue was taken up in 30 ml of water and dehydrohalogenated by means of an ion exchanger (Dowex 50 WX 8). The thus obtained aqueous solution of the free (R)-α-methylmethionine was evaporated and the crystalline residue dried at 50° C. to constant weight in a vacuum. Yield 0.402 gram (88% of theory).
$[\alpha]_D^{25}$= −17.9° (c=0.7; 0.2N HCl).
¹H-NMR (D₂O): 2.83-2.56 (m, 2H) S—CH₂; 2.32-2.03 (m, 2H) C—CH₂; 2.23 (s, 3H) S—CH₃; 1.63 ppm (s, 3H) C—CH₃.
Reference (HDO): 4.90 ppm.

Example 3

(a) Production of (S)-N-(2',2'-dimethyl-propylidene)-alanine monomethylamide There were added 33.0 ml (300 mmols) of pivalaldehyde to 30.1 grams (295 mmols) of (S)-alanine monomethylamide dissolved in 100 ml of n-pentane. The reaction mixture was boiled at a water separator until the formation of water was ended (3.5 hours). The solvent was removed under reduced pressure and there remained behind 44.0 grams (88% of theory) of (S)-N-(2',2'-dimethyl-propylidene)-alanine monomethylamide, which could be further worked without purification. To ascertain the exact material data, a test sample was purified by distillation.

Boiling Point: 140° C./0.065 mbar.
$[\alpha]_{365}^{20}$: +219.6° (c=5.3; CHCl$_3$).

|  | % C | % H |
|---|---|---|
| Calculated: | 63.49 | 10.66 |
| Found: | 63.57 | 10.74 |

IR (CHCl$_3$): 3330 (m), 2980 (s), 1665 (s), 1520 (m), 1415 (m) cm$^{-1}$.

$^1$H-NMR (CDCl$_3$): 7.57 (s, 1H) H—C=N; 6.98 (s, 1H) N—H; 3.67 (q, J=7 Hz, 1H) C—H; 2.84 (d, J=5 Hz, 3H) CH$_3$—N; 1.30 (d, J=7 Hz, 3H) CH$_3$—C; 1.06 ppm (s, 9H) (CH$_3$)$_3$—C.

(b) Production of (2S,5S)-1-Benzoyl-2-tert.butyl-3,5-dimethyl-imidazolidine-4-one A solution of 13.6 grams (80.0 mmole) of the (S)-N-(2',2'-dimethylpropylidene)-alanine monomethylamide produced according to (a) in 30 ml of methanol was treated with cooling to 0° C. with 60 ml of a saturated methanolic hydrochloric acid and stirred for 30 minutes at 0° C. and subsequently for 2 hours at 25° C. The solvent was removed at 25° C. under reduced pressure and the residue taken up in 100 ml of methylene chloride. The methylene chloride solution was treated at 0° C. with 9.3 ml (80 mmoles) of benzoyl chloride and 22.2 ml (160 mmoles) of triethylamine. After heating to 25° C. the reaction mixture was washed twice, each time with 150 ml of 2N soda solution (aqueous sodium carbonate) and once with 100 ml of water. The organic phase was dried over MgSO$_4$, the methylene chloride distilled off in a vacuum and the residue dried for 1 hour at 50° C. and 0.065 mbar. Yield of (2S,5S)-1-benzoyl-2-tert.butyl-3,5-dimethyl-imidazolidine-4-one: 21.0 grams (96% of theory). The product was recrystallized twice from diethyl ether for purification.

Melting Point: 175° C.
$[\alpha]_D^{25}$: +44.5° (c=1.0; CHCl$_3$).

IR (KBr): 2980 (m), 1700 (s), 1365 (s), 1380 (s), 1260 (m) cm$^{-1}$.

|  | % C | % H | % N |
|---|---|---|---|
| Calculated: | 70.04 | 8.08 | 10.21 |
| Found: | 69.96 | 8.16 | 10.23 |

$^1$H-NMR (CDCl$_3$): 7.93–7.30 (m, 5H) H$_{Ar}$; 5.67 (s, 1H) CH; 4.27 (q, J=7 Hz, 1H) CH—CH$_3$; 3.04 (s, 3H) CH$_3$—N; 1.05 (s, 9H) (CH$_3$)$_3$—C; 0.97 ppm (d, J=7 Hz, 3H) CH$_3$—CH.

(c) Production of (2S,5S)-1-Benzoyl-2-tert.butyl-5-(3',4'-dimethoxybenzyl)-3,5-dimethyl-imidazolidine-4-one There were added to 2.74 grams (10.0 mmoles) of the (2S,5S)-1-benzoyl-2-tert.butyl-3,5-dimethyl-imidazolidine-4-one produced according to (b) and dissolved in 60 ml of tetrahydrofuran at −78° C. 11 mmoles of a 1 molar solution of n-butyllithium in n-hexane. Thereby the solution became deeply red in color. After stirring for a further 15 minutes at −78° C. there were added 2.8 grams (12 mmoles) of 3,4-dimethoxybenzyl bromide dissolved in 15 ml of tetrahydrofuran. The reaction mixture as allowed to warm to room temperature. The now weakly yellow reaction mixture was poured into 100 ml of an about half saturated aqueous NH$_4$Cl solution and extracted with, in all, 200 ml of diethyl ether. The combined organic extracts were washed with water, dried over MgSO$_4$ and freed from solvent under reduced pressure. For further purification the residue was chromotagraphed with a mixture of diethyl ether and n-pentane in a volume ratio of 1:1 as mobile phase. After the evaporation of the solvent from the eluate there remained behind 2.64 grams (61% of theory) of (2S,5S)-1-benzoyl-2-tert.butyl-5-(3',4'-dimethoxybenzyl)-3,5-dimethyl-imidazolidine-4-one.

Melting Point: 165° C.
$[\alpha]_D^{25}$: +74.9° (c=0.4; CHCl$_3$).

IR (KBr): 2960 (m), 1710 (s), 1640 (s), 1520 (s), 1370 (m), 1260 (m), 1240 (m), 1135 (m) cm$^{-1}$.

MS: 424 (M+,0.5), 105 (100).

$^1$H-NMR (CDCl$_3$): 7.80–6.67 (m, 8H) H$_{Ar}$; 5.26; 4.92 (s, 1H) C—H; 3.90; 3.51 (s, 3H) CH$_3$—O; 3.83 (s, 3H) CH$_3$—O; 3.80–3.00 (m, 2H) C—CH$_2$; 2.97; 2.63 (s, 3H) CH$_3$—N; 2.90; 2.60 (s, 3H) CH$_3$—C; 1.00; 0.70 ppm (s, 9H) (CH$_3$)$_3$—C.

(d) Production of (S)-α-methyl-N-acetyl-β-(3',4'-diacetoxyphenyl)-alanine (trisacetyl derivative of (S)-α-methyldopa)

4.69 grams (11.05 mmoles) of the (2S,5S)-1-benzoyl-2-tert.butyl-5-(3',4'-dimethoxybenzyl)-3,5-dimethyl-imidazolidine-4-one produced according to (c) were heated in a bomb tube at 180° C. for 4 hours with 30 ml of 20 weight percent aqueous hydrochloric acid. The hydrolysis mixture was filtered, extracted with 30 ml of methylene chloride and the aqueous phase evaporated to dryness in a vacuum. The residue was taken up in 20 ml of pyridine and again evaporated to dryness at 0.01 mbar. To the now remaining residue were added 40 ml of acetic anhydride and 20 ml of pyridine. The mixture was heated for 3 hours to 95° C. and subsequently again evaporated to dryness. The remaining oil was dissolved in 10 ml of water, 5 ml of acetone and 1 ml of 2.5 molar hydrochloric acid. The mixture again was evaporated and the now remaining residue was dissolved in 20 ml of ethanol. The solution was added to a mixture of 50 ml of water and 150 ml of diethyl ether. The aqueous phase was extracted twice, each time with 100 ml of diethyl ether. The ether phases were combined and the diethyl ether was evaporated. The residue was recrystallized from a mixture of acetone and n-pentane in a volume ratio of 1:1. The yield of the trisacetyl derivative of (S)-α-methyldopa was 2.44 grams (56% of theory).

Melting Point: 178°–179° C. (according to the literature: 180°–181° C.).

$[\alpha]_D^{25}$: −93.9° (c=1.04; CH₃OH).

¹H-NMR (CD₃OD): 7.20–6.91 (m, 3H) H$_{Ar}$; 4.85 (s, 2H) NH, COOH; 3.46; 3.11 (AB, J=13.5 Hz, 2H) 2xC—H; 2.21 (s, 6H) 2xOOC—CH₃; 1.90 (s, 3H) NH—CO—CH₃; 1.40 ppm (s, 3H)—C—CH₃.

Example 4

(a) Production of (S)-N-(2',2'-dimethyl-propylidene)-alanine monomethylamide

The monomethylamide was produced as described in example 3(a).

(b) Production of (2R,5S)-1-Benzoyl-2-tert.butyl-3,5-dimethyl-imidazolidine-4-one 13.6 grams (80 mmoles) of the (S)-N-(2',2'-dimethyl-propylidene)-alanine monomethylamide produced according to (a) were heated with 20.0 grams (88 mmoles) of benzoic anhydride for 3 hours at 130° C. After cooling off the solidified mass was taken up in 200 ml of methylene chloride and the methylene chloride solution washed twice, each time with 150 ml of 2N soda solution and once with 100 ml of water. The organic phase was dried over MgSO₄ and the methylene chloride distilled off under reduced pressure. The residue was recrystallized twice from a mixture of diethyl ether and methylene chloride in a volume ratio of 1:1. The yield of (2R,5S)-1-benzoyl-2-tert.butyl-3,5-dimethyl-imidazolidine-4-one was 20.0 grams (91% of theory).

Melting Point: 114°–117° C.

$[\alpha]_D^{25}$: −47.7° (c=1.04; CHCl₃).

IR (KBr): 2980 (m), 1700 (s), 1665 (s), 1630 (m), 1360 (s) cm⁻¹.

|  | % C | % H | % N |
|---|---|---|---|
| Calculated: | 70.04 | 8.08 | 10.21 |
| Found: | 69.99 | 8.11 | 10.16 |

¹H-NMR (CDCl₃): 7.40 (s, 5H) H$_{Ar}$; 5.60 (s, 1H) CH; 3.83 (q, J=7 Hz, 1H) CH—CH₃; 3.02 (s, 3H) CH₃—N 2.42 (d, J=7 Hz, 3H) CH₃—CH 1.10 ppm (s, 9H) (CH₃)₃—C.

(c) Production of (2R,5R)-1-benzoyl-2-tert.butyl-5-(3',4'-dimethoxybenzyl)-3,5-dimethyl-imidazolidine-4-one There were added at −78° C. 11 mmoles of a 1 molar solution of lithium diisoproylamide in tetrahydrofuran to 2.74 grams (10.0 mmoles) of the (2R,5S)-1-benzoyl-2-tert.butyl-3,5-dimethyl-imidazolidine-4-one produced according to (b) and dissolved in 60 ml of tetrahydrofuran. Thereby the solution became deeply red in color. After stirring for 30 minutes at −78° C. there were added 2.8 grams (12.0 mmoles) of 3,4-dimethoxybenzyl bromide dissolved in 15 ml of tetrahydrofuran. The reaction mixture was allowed to warm to room temperature in the course of 2 hours. The now weakly yellow reaction mixture was poured into 100 ml of an about half saturated aqueous NH₄Cl solution and extracted with, in all, 400 ml of diethyl ether. The combined organic extracts were washed with water, dried over MgSO₄ and freed from solvent under reduced pressure. For further purification the residue was chromatographed with a mixture of diethyl ether and n-pentane in a volume ratio of 5:1 as mobile phase. After the evaporation of the solvent from the eluat there remained behind 2.47 grams (57% of theory) of (2R,5R)-1-benzoyl-2-tert.butyl-5-(3',4'-dimethoxybenzyl)-3,5-dimethyl-imidazolidine-4-one.

Melting Point: 165° C.

$[\alpha]_D^{25}$: −78.0° (c=0.5; CHCl₃).

IR (KBr): 2960 (m), 1640 (s), 1520 (m), 1370 (m), 1260 (m), 1240 (m), 1135 (m) cm⁻¹.

¹H-NMR (CDCl₃): 7.80–6.67 (m, 8H) H$_{Ar}$; 5.26; 4.92 (s, 1H) C—H; 3.90; 3.51 (s, 3H) O—CH₃; 3.83 (s, 3H) O—CH₃; 3.80–3.00 (m, 2H) C—CH₂; 2.97–2.60 (s, 3H) C—CH₃; 1.00; 0.77 ppm (s, 9H)—C—(CH₃)₃.

(d) Production of (R)-α-methyl-β-(3',4'-dihydroxyphenyl)-alanine ((R)-α-methyldopa)

0.6 gram (1.41 mmoles) of the (2R,5R)-1-benzoyl-2-tert.butyl-5-(3',4'-dimethoxybenzyl)-3,5-dimethyl-imidazolidine-4-one produced according to (c) was heated in a bomb tube at 180° C. for 4 hours with 20 ml of 20 weight percent aqueous hydrochloric acid. The hydrolysis mixture was filtered, extracted with 15 ml of methylene chloride and the aqueous phase evaporated to dryness at 20 mbar. There remained 0.47 gram of (R)-α-methyldopa in the form of the methylammonium salt.

¹H-NMR (D₂O): 6.91–6.50 (m, 3H) H$_{Ar}$; 3.10; 2.86 (AB, J=13.5 Hz, 2H) 2xC—H; 2.53 (s, 3H) CH₃—N; 1.55 ppm (s, 3H) C—CH₃.

The entire disclosure of German priority application No. P 33 34 855.3 is hereby incorporated by reference.

What is claimed is:

1. A process for the enantioselective production of α-aminocarboxylic acids of the formula $$R^2-\underset{\underset{NH_2}{|}}{\overset{\overset{R^1}{|}}{C^*}}-COOH \quad (I)$$

where * is a center of asymmetry, R¹ is methyl, ethyl, n-propyl, n-butyl, allyl, benzyl, or a methyl, ethyl, propyl, isopropyl, butyl, sec. butyl, amyl, hexyl, methoxy, ethoxy, propoxy or butoxy substituted benzyl group and R² is a methyl, ethyl, n-propyl, i-propyl, n-butyl, secondary butyl, i-butyl, methoxymethyl, methylmercaptomethyl, 2-methylmercaptoethyl, 2-ethylmercaptoethyl, phenyl, or benzyl or a phenyl group substituted on the ring with 1 to 3 alkyl or alkoxy groups or a benzyl group substituted on the ring with 1 to 3 alkyl or alkoxy groups, fluorine or bromine comprising acid saponifying an imidazolidin-4-one of the formula $$H_3C-\underset{\underset{CH_3}{|}}{\overset{\overset{CH_3}{|}}{C}}-HC^*\underset{\underset{\underset{Aryl}{\diagdown}}{\diagup}}{\overset{\overset{\overset{R^3}{|}}{N-C=O}}{\diagdown}}\underset{\overset{C}{\diagdown}}{\overset{\underset{\diagdown R^2}{\diagup}}{\underset{O}{\diagup}}}\overset{R^1}{\underset{}{}}$$

wherein R³ is methyl or ethyl.

2. A process according to claim 1 including the step of forming the imidazolidin-4-one of formula (II) by alkylating an enolate of the formula

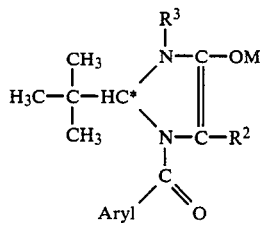
(III)

where M is lithium, sodium, or potassium with an alkylating agent of the formula $$R^1—X \qquad (IV)$$

where X is a group that is selected from the group consisting of chloride, bromide, iodide, tosylate, methylate, or trifluoromethyl-sulfonate.

3. A process according to claim 2 including the step of forming the enolate of formula (III) by reacting an imidazolidin-4-one of the formula

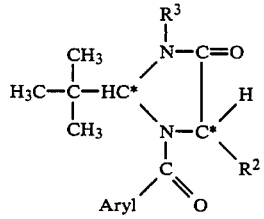
(V)

with a strong base of the formula

M—Y where Y is hydrogen or an n-butyl, tert.butylate, amino, dimethylamino, diethylamino, di-n-propylamino, diisopropylamino, di(trimethylsilyl)amino or phenyl group.

4. A process according to claim 1 including the step of forming the enolate of formula (III) by reacting an imidazolidin-4-one of the formula

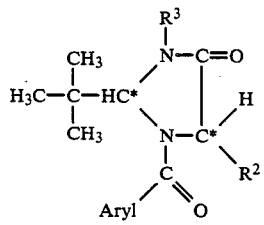
(V)

with a strong base of the formula

M—Y where Y is hydrogen or an n-butyl, tert.butylate, amino, dimethylamino, diethylamino, di-n-propylamino, diisopropylamino, di(trimethylsilyl)-amino or phenyl group.

5. A process according to claim 4 including the step of of forming the imidazolidin-4-one of formula (V) by cyclizing an imine of the formula

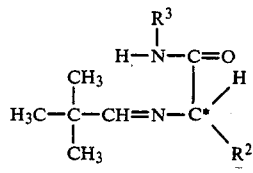
(VII)

with simultaneous or subsequent introduction of the group

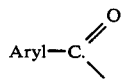

6. A process according to claim 3 including the step of of forming the imidazolidin-4-one of formula (V) by cyclizing an imine of the formula

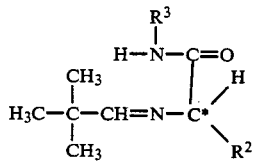
(VII)

with simultaneous or subsequent introduction of the group

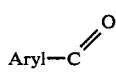

7. A process according to claim 6 including the step of forming the imine of formula VII by reacting an α-aminocarboxylic acid amide of the formula

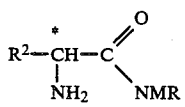
(VIII)

with pivalaldehyde.

8. A process according to claim 5 including the step of forming the imine of formula VII by reacting an α-aminocarboxylic acid amide of the formula

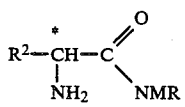
(VIII)

with pivalaldehyde.

9. A process according to claim 1 comprising carrying out the saponification at a temperature of 150° to 200° C. under pressure.

10. A process according to claim 9 comprising carrying out the saponification with concentrated mineral acid.

11. A process according to claim 10 wherein the mineral acid is hydrochloric acid, hydrobromic acid or sulfuric acid.

12. A process according to claim 2 comprising carrying out the alkylation at a temperature between −80° and 0° C.

13. A process according to claim 12 wherein there is employed a 1.1 to 1.2 fold molar excess of the alkylating agent (IV) based on the original imidazolidin-4-one of formula (V).

14. A process according to claim 3 comprising carrying out the reaction at a temperature between −80° and 0° C.

15. A precess according to claim 14 wherein there is employed 1.0 to 1.1 equivalents of strong base per mole of imidazolidin-4-one.

16. A process according to claim 4 comprising carrying out the reaction at a temperature between −80° and 0° C. and wherein there is employed 1.0 to 1.1 equivalents of strong base per mole of imidazolidin-4-one.

17. A process according to claim 5 wherein the cyclization is carried out at a temperature between 110° and 150° C. with benzoic anhydride in an amount of 1.0 to 1.2 based on the imine and in the absence of a solvent.

18. A process according to claim 6 wherein the cyclization is carried out with methanolic hydrochloric acid at a temperature between −10° and +40° C.

19. A process according to claim 7 comprising reacting the α-aminocarboxylic acid amide with the pivalaldehyde by boiling in an inert solvent and removing the water formed.

20. A process according to claim 8 comprising reacting the α-aminocarboxylic acid amide with the pivalaldehyde by boiling in an inert solvent and removing the water formed.

* * * * *